United States Patent
Hawkins et al.

(10) Patent No.: US 6,387,113 B1
(45) Date of Patent: May 14, 2002

(54) METHOD AND APPARATUS FOR REPAIRING A TORN MENISCUS

(75) Inventors: H. Gene Hawkins, Warsaw; David R. Sarver, Logansport, both of IN (US)

(73) Assignee: Biomet, Inc., Warsaw, IN (US)

( * ) Notice: Subject to any disclaimer, the term of this patent is extended or adjusted under 35 U.S.C. 154(b) by 0 days.

(21) Appl. No.: 09/496,797

(22) Filed: Feb. 2, 2000

Related U.S. Application Data
(60) Provisional application No. 60/118,277, filed on Feb. 2, 1999.

(51) Int. Cl.$^7$ ................................................ A61B 17/04

(52) U.S. Cl. ...................... 606/219; 606/142; 227/180.1

(58) Field of Search ................................ 606/219, 220, 606/142, 143; 227/19, 180.1

(56) References Cited

U.S. PATENT DOCUMENTS

| | | | | |
|---|---|---|---|---|
| 4,349,028 A | * | 9/1982 | Green | 227/19 |
| 4,402,445 A | * | 9/1983 | Green | 227/19 |
| 4,724,839 A | * | 2/1988 | Bedi et al. | 606/219 |
| 4,873,976 A | | 10/1989 | Schreiber | |
| 4,895,148 A | | 1/1990 | Bays et al. | |
| 4,924,865 A | | 5/1990 | Bays et al. | 606/77 |
| 4,976,715 A | | 12/1990 | Bays et al. | |
| 4,994,073 A | * | 2/1991 | Green | 606/219 |
| 4,997,436 A | | 3/1991 | Oberlander | 606/142 |
| 5,002,562 A | | 3/1991 | Oberlander | 606/221 |
| 5,108,422 A | * | 4/1992 | Green et al. | 606/219 |
| 5,154,189 A | | 10/1992 | Oberlander | 128/898 |
| 5,292,334 A | * | 3/1994 | Howansky | 606/220 |

FOREIGN PATENT DOCUMENTS

| | | | | |
|---|---|---|---|---|
| DE | 2901983 A | * | 7/1980 | A01G/23/08 |

OTHER PUBLICATIONS

Bionx Implants, Inc. Surgical Technique, "Meniscus Arrow", Feb. 1998, 4 sheets.
Investor's Business Daily, "For People Who Choose to Succeed," Bionx Implants, Inc. /Blue Bell, Pennsylvania, "Implant Revolutionizing Knee Treatment", copyright 1997, 1 sheet.
"Meniscal Arrow", Techniques in Orthopaedics, vol. 13, No. 2, 1998, Brad Cohen, M.D. and James Tasto, M.D., copyright 1998.
"Failure Strength of a New Meniscus Arrow Repair Technique: biomechanical Comparison With Horizontal Suture"; Arthroscopy: The Journal of Arthroscopic and Related Surgery, vol. 13, No. 2 (Apr.), 1997: pp 183–187.
"Meniscal Stapler", Surgical Dynamics, Inc. copyright 1997, 2 sheets.
"Preliminary Results of the T–Fix Endoscopic Meniscus Repair Technique in an Anterior Cruciate Ligament Reconstruction Population"; Arthroscopy: The Journal of Arthroscopic and Related Surgery, vol. 13, No. 2 (Apr.), 1997: pp. 218–223.

(List continued on next page.)

*Primary Examiner*—Gary Jackson
(74) *Attorney, Agent, or Firm*—Harness, Dickey & Pierce, P.L.C.

(57) ABSTRACT

A method and apparatus for repairing a torn meniscus during an arthroscopic surgical procedure includes a surgical staple and a pneumatic powered implant device. The surgical staple includes a pair of legs and a connection member retaining the pair of legs in a substantial parallel alignment. The pneumatic powered implant device is a portable and disposable device that can easily implant the surgical staple at any desired location during an arthroscopic surgical procedure. The pneumatic powered implant device also includes several quick disconnect barrels having different shapes providing the surgeon with the option of how to position the implant device during the arthroscopic surgical procedure.

18 Claims, 7 Drawing Sheets

OTHER PUBLICATIONS

Technical Note "Use of the T–Fix Suture Anchor In Fascial Sheath Reconstruction of Complex Meniscal Tears"; Arthroscopy: The Journal of Arthroscopy and Related Surgery, vol. 12, No. 2 (Apr.), 1996: pp 251–255.

Everything You Need for Complete Meniscal Repair, "Meniscus Menter II," Instrument Makar, Inc.; 1 sheet.

Target Any Zone; "The New BioStinger Bio–absorbable Meniscal Fixation System Stings The Competition"; Linvatec, copyright 1998, 1 sheet.

"Meniscal Fixation with an Absorbable Staple," Knee Surg., SportsTraumatol, Arthroscopy (1997) pp. 22–30.

"Knee Arthroscopy, Diagnosing and Treating Your Problem," brochure, copyright 1992, 1995 by Krames Communications, pp. 1–8.

Arthrex; "Mobile Meniscus Suturing System," Arthroscopic Technique In–Service Manual; 4 sheets.

Meniscus Arrow "The Ideal System For Meniscus Repair," 4 sheets.

* cited by examiner

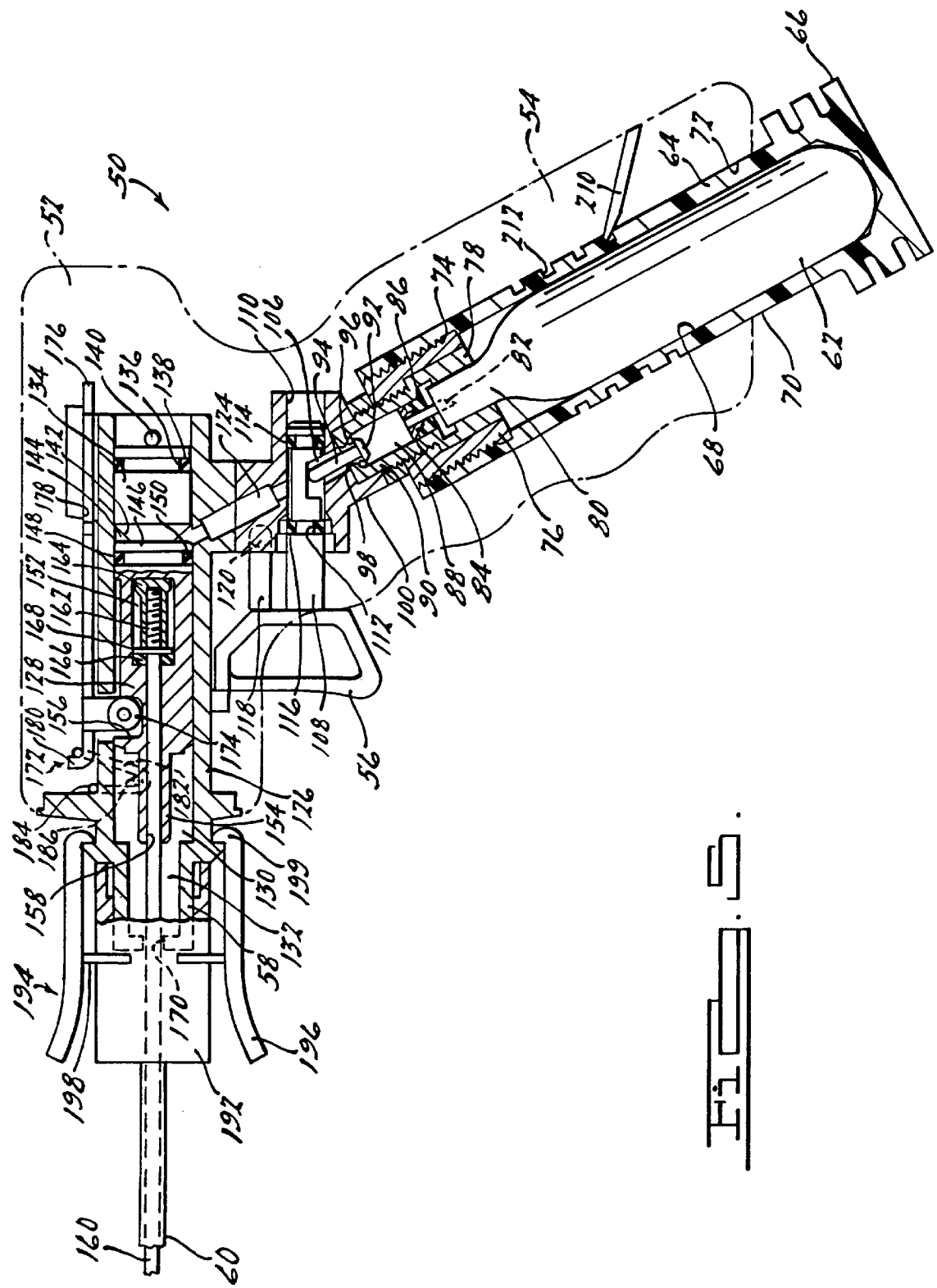

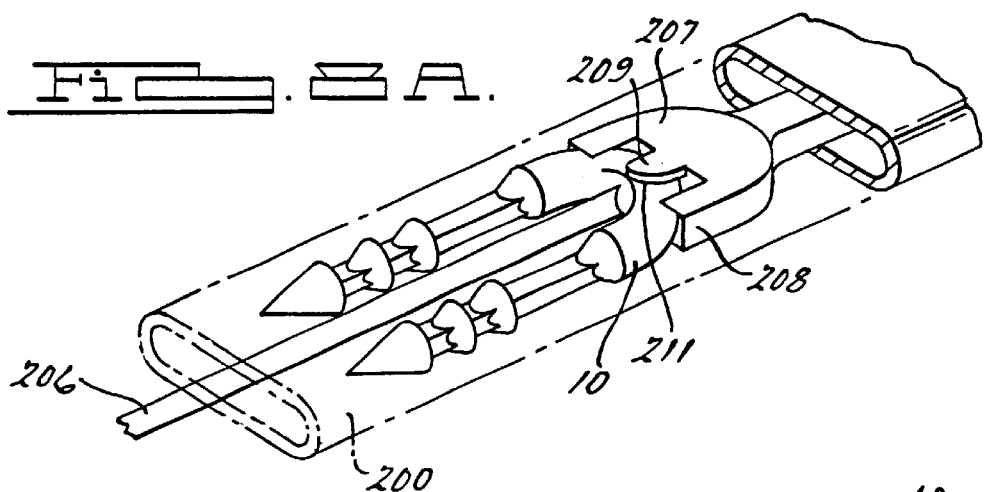
FIG. 8A.
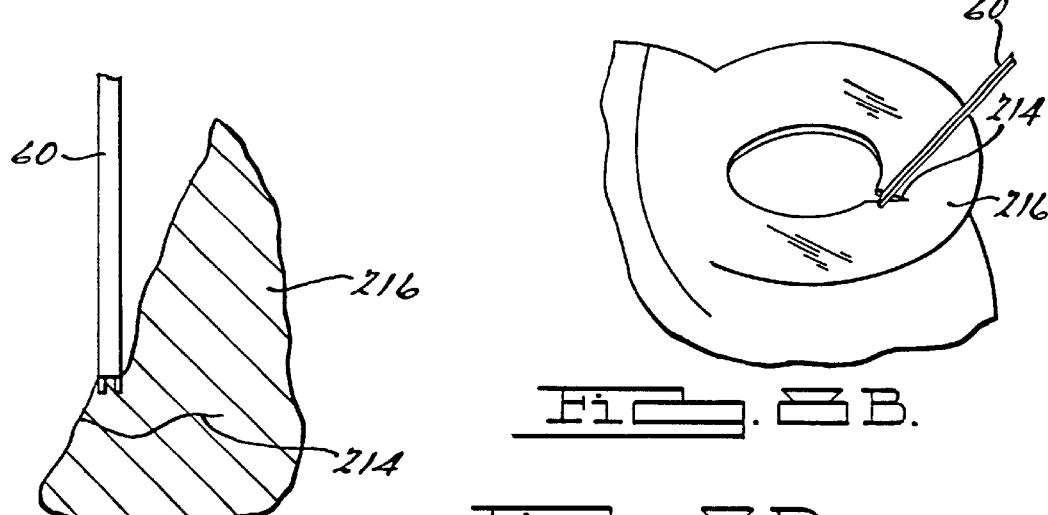
FIG. 8B.
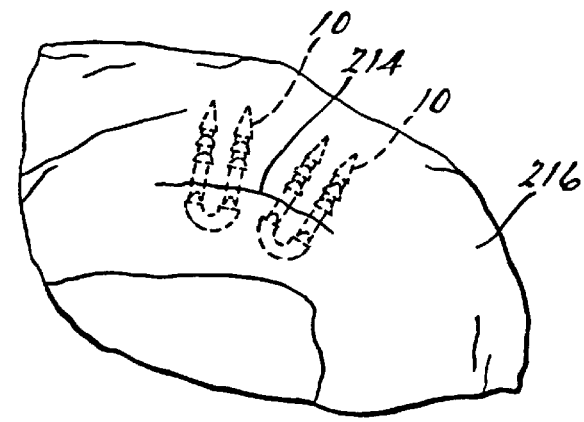
FIG. 8C.
FIG. 8D.
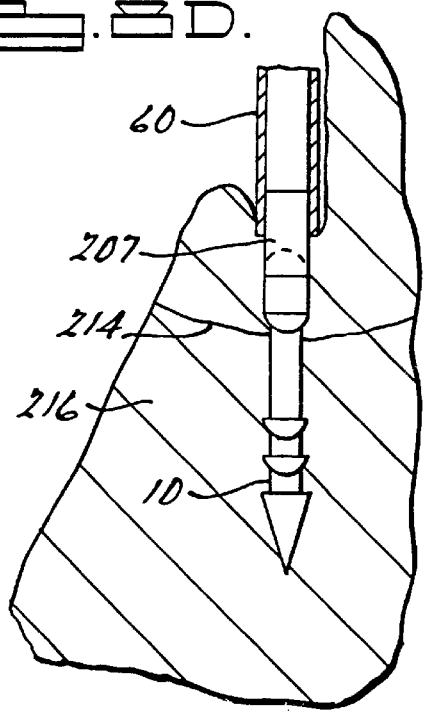
FIG. 8E.

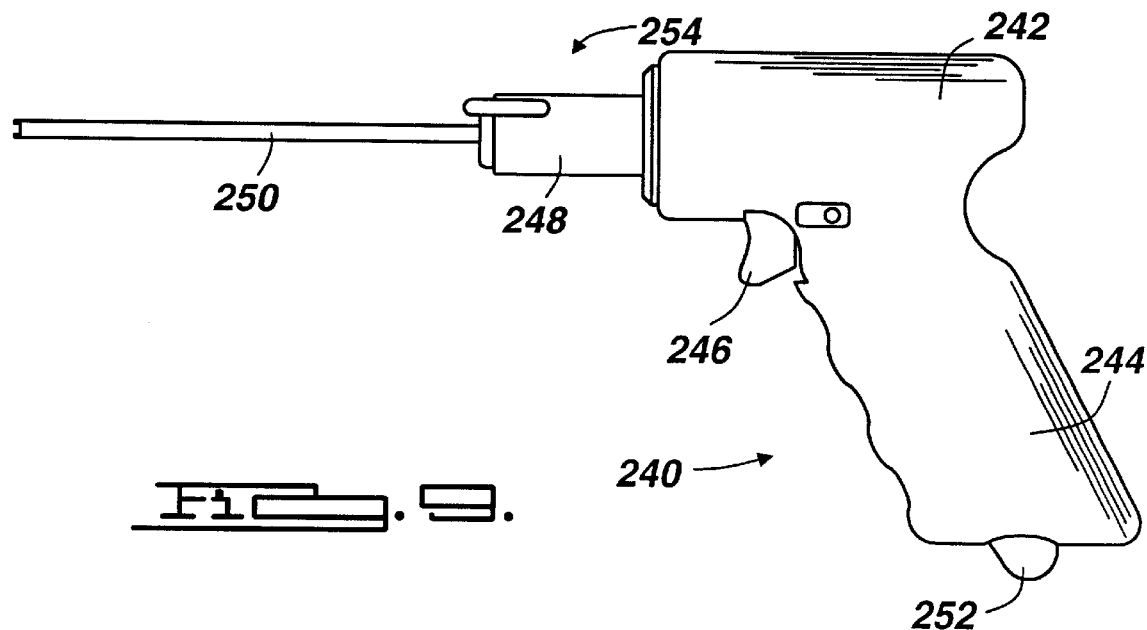
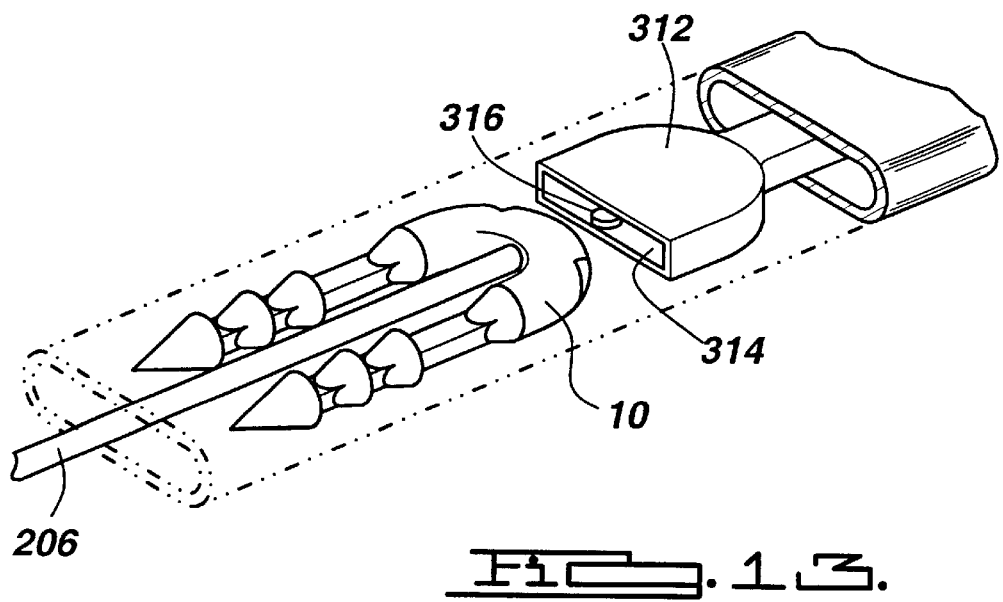

METHOD AND APPARATUS FOR REPAIRING A TORN MENISCUS

CROSS-REFERENCE TO RELATED APPLICATIONS

This application claims priority to provisional Application No. 60/118,277, filed on Feb. 2, 1999, and entitled "Method and Apparatus For Repairing A Torn Meniscus."

BACKGROUND OF THE INVENTION

1. Field of the Invention

This invention relates generally to a method and apparatus for use in repairing soft tissue, and more particularly, to a method and apparatus for repairing a torn meniscus during arthroscopic surgery.

2. Discussion of the Related Art

There are many techniques employed to repair damaged soft tissue. These techniques include suturing, stapling, taping and the like. Selection of which technique to employ depends upon the type of soft tissue being repaired, the soft tissue location, and the required strength of the repair. While there exists many techniques to repair soft tissue, there is a growing need to easily and quickly repair a torn meniscus in the knee during arthroscopic surgery.

The meniscus tissue is a fibrocartilaginous structure in the knee joint which performs multiple critical functions, including contributing to normal knee biomechanics and the general well-being of the joint. Generally, the menisci are comprised of two (2) C-shaped fibrocartilaginous structures residing on the tibial plateau. The peripheral rim of a meniscus is thick, tapering to a thin, free inner border. The superior surface is concave to contact the femoral condyles, while the inferior surface is flat to contact the tibial plateau. The fibers forming the menisci are mainly oriented circumferentially throughout the meniscus, parallel to the peripheral border, to withstand hoop stresses placed upon the meniscus by the femoral condyles. It is generally recognized that repair of meniscal lesions, to the extent possible, is preferable to excision so as to attempt to maintain the normality of the meniscus and have it continue to function as intended.

One technique used to repair a torn meniscus is by means of suturing the tear by use of a suture and suture needle. However, a disadvantage with this type of technique is that suturing is relatively time consuming and very labor intensive. Moreover, a great deal of experience is generally required to efficiently repair a torn meniscus using a suture and suture needle. Other techniques involve implanting surgical fasteners using a spring gun. One disadvantage associated with utilizing a surgical fastener is the potential for the surgical fastener to migrate once it has been implanted which could potentially cause patient discomfort. Another disadvantage is directed to the spring gun which generally requires a trigger force that exceeds the spring strength, as well as creates a significant spring recoil once the spring gun is triggered.

What is needed then is a method and apparatus for repairing a torn meniscus which does not suffer from the above-mentioned disadvantages. This, in turn, will reduce the surgical time, complexity and cost, provide a surgical fastener that prohibits migration in the meniscus, provide a portable pneumatic implant device that eliminates spring recoil and reduces trigger resistance while providing sufficient velocity to fully seat the surgical fastener, and provide an implant device that may be readily modified depending on the surgical application and repair required. It is, therefore, an object of the present invention to provide such a method and apparatus for repairing a torn meniscus during an arthroscopic surgical procedure.

SUMMARY OF THE INVENTION

In accordance with the teachings of the present invention, a method and apparatus for repairing a torn meniscus during an arthroscopic surgical procedure is disclosed. In this regard, a surgical staple having a pair of legs and a rigid connecting member retaining the legs in a parallel orientation is used to repair the torn meniscus. A portable pneumatic powered implant device is used to easily implant the surgical staple at the desired location during the arthroscopic surgical procedure. The pneumatic powered implant device includes several quick disconnect barrels having different shapes to provide a surgeon with different surgical options.

In one preferred embodiment, a pneumatic powered implant gun drives an implant into a patient. The pneumatic powered implant gun includes a drive shaft, a barrel, a pressurized gas source and a trigger mechanism. The drive shaft is operable to drive the implant into the patient. The barrel slidably receives the drive shaft to guide the implant to a target site. The pressurized gas source is operable to retain pressurized gas. The trigger mechanism releases at least a portion of the pressurized gas to drive the drive shaft along the barrel to drive the implant into the target site.

In another preferred embodiment, a surgical staple for use in repairing tissue in a patient includes a first leg, a second leg and a connection member. The first leg has a first proximal end and a first distal end. The second leg has a second proximal end and a second distal end. The connection member is substantially rigid and operable to substantially retain the first leg relative to the second leg.

In yet another preferred embodiment, a method for driving an implant into a patient is disclosed. This method includes loading an implant within a barrel of pneumatic powered implant gun, engaging the implant with a drive shaft slidably disposed within the barrel, and releasing pressurized gas to drive the drive shaft along the barrel to drive the implant into the patient.

Use of the present invention provides an improved method and apparatus for repairing a torn meniscus during arthroscopic surgical procedures. As a result, the aforementioned disadvantages associated with the currently available methods and techniques for repairing a torn meniscus, as well as other types of soft tissue have been substantially reduced or eliminated.

BRIEF DESCRIPTION OF THE DRAWINGS

Still other advantages of the present invention will become apparent to those skilled in the art after reading the following specification and by reference to the drawings in which:

FIG. 5 is a side cross-sectional view of the pneumatic powered implant device of FIG. 4;

FIGS. 8A–8E illustrate a method for implanting the surgical staple according to the teachings of the present invention;

FIG. 9 is a side elevational view of a pneumatic powered implant device according to the teachings of another preferred embodiment of the present invention;

FIG. 13 is a perspective view of a cradle for engaging a surgical staple according to the teachings of another preferred embodiment in the present invention.

DETAILED DESCRIPTION OF THE PREFERRED EMBODIMENT(S)

The following description of the preferred embodiment concerning a method and apparatus for repairing a torn meniscus during an arthroscopic surgical procedure is merely exemplary in nature and is not intended to limit the invention or its application or uses. Moreover, while the present invention is described in detail below with reference to repairing a torn meniscus utilizing a surgical staple, it will be appreciated by those skilled in the art that the present invention is clearly not limited to merely repairing a torn meniscus with a surgical staple but may include repairing any type of tissue injury using various types of surgical fasteners.

Figure 1:
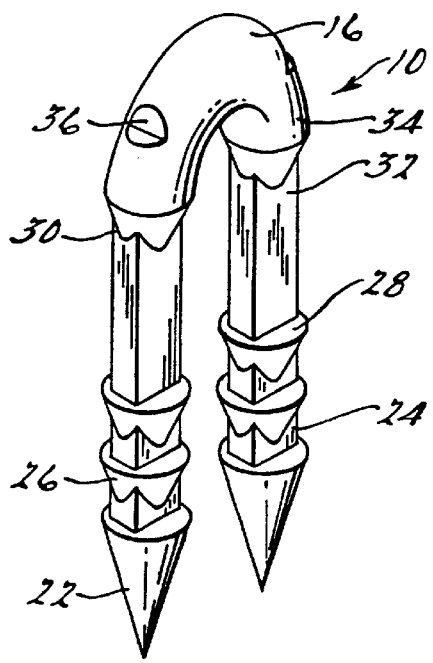
FIG. 1 is a perspective view of a surgical staple according to the teachings of the present invention.
Figure 2:
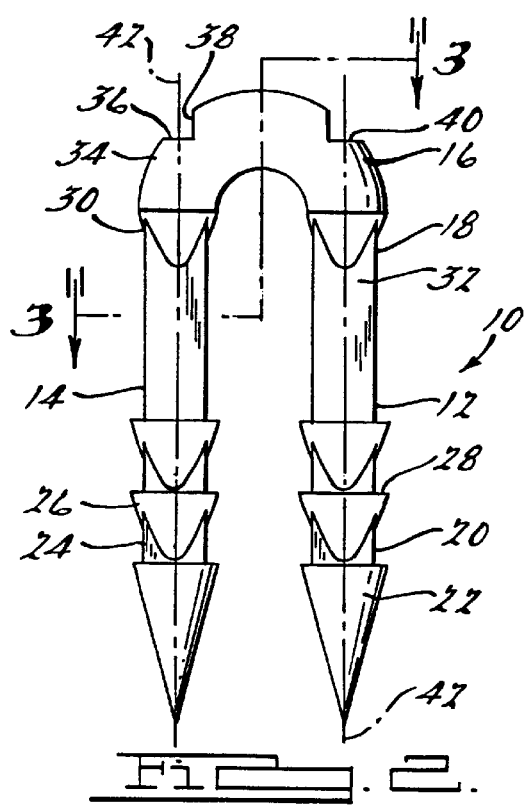
FIG. 2 is a side elevational view of the surgical staple of FIG. 1.
Figure 3:
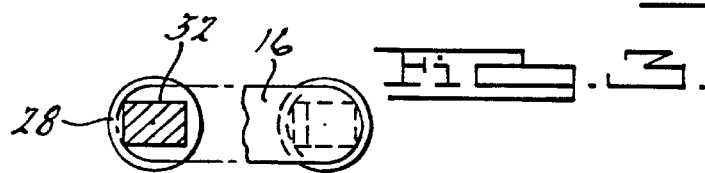
FIG. 3 is a cross-sectional view of the surgical staple of FIG. 1 taken along line 3—3 of FIG. 2.

Referring to FIGS. 1–3, a surgical staple or fastener 10 for repairing a torn meniscus or any other type of soft tissue is shown. The surgical staple 10 is a one piece injection molded unit formed from a resorbable material. Preferably, the surgical staple 10 is formed from a resorbable material marketed under the trademark LactoSorb® and offered by Biomet, Inc. of Warsaw, Ind. However, any other appropriate type of biocompatible material, including other resorbable materials, as well as various types of stainless steel, titanium, etc. may also be used.

The surgical staple 10 includes a first leg 12, a second leg 14 and a substantially rigid connection member 16 that retains the first leg 12 substantially parallel to the second leg 14. Each leg 12 and 14 includes a proximal end 18 and a distal end 20. Located at the distal end 20 of each leg 12 and 14 is a conically shaped spear member 22. Extending axially from each of the spear members 22 is a substantially rectangular body 24 that extends from the distal end 20 to the proximal end 18. Adjacent to each spear member 22 are a plurality of conically shaped barbs 26 that extend out from the rectangular body 24. The spear members 22 piercingly engage the soft tissue or meniscus while the annular engagement regions 28 of the spear members 22 and barbs 26 resist axial removal of the surgical staple 10 once it has been implanted into the soft tissue. A transition region 30 is shown at the proximal end 18 of each of the rectangular bodies 24. The transition region 30 transitions from a substantially rectangular shape having a substantially rectangular outer sidewall 32 to a substantially circular shape having a circular outer sidewall 34 at the connection member 16.

The connection member 16 is substantially U-shaped and extends from the proximal end 18 of the first leg 12 and the second leg 14 of the surgical staple 10. The connection member 16 includes a pair of notch regions 36 defined by a horizontal sidewall 38 and a vertical sidewall 40. Each vertical sidewall 40 is substantially centered along each longitudinal axis 42 of each leg 12 and 14. In this regard, each vertical sidewall 40 is used as the engagement face for the impact force applied to the surgical staple 10 upon implanting the surgical staple 10 into soft tissue. For example, an engagement member from an implant device, further discussed herein, will engage the vertical engagement faces 40, so that the impact force is directed along each axis 42 of each leg 12 and 14. This enables the surgical staple 10 to be implanted with the first leg 12 remaining substantially parallel to the second leg 14. The horizontal sidewalls 38 are sized appropriately so that an interference fit is created to removably retain the surgical staple 10 within the implant device once a surgical staple 10 is loaded into the implant device.

Referring now to FIGS. 4–7, a pneumatic powered implant device or gun 50 according to the teachings of a first preferred embodiment in the present invention is shown. The pneumatic powered implant gun 50 is a portable self-contained disposable unit used for implanting the surgical staple 10 or any other surgical device. The implant gun 50 includes a body 52 having a handle 54, a trigger 56 and a chuck 58. Extending from the chuck 58 is a first removable barrel 60 that is removably coupled to the chuck 58. The body 52 of the implant gun 50 is preferably formed from ABS plastic which provides for a substantially light weight implant gun 50 that is easy to handle and maneuver during a surgical procedure. The implant gun 50 may also be formed from any other appropriate material.

Adjustably retained within the handle 54 of the implant gun 50 is a $CO_2$ cartridge 62. The $CO_2$ cartridge 62 provides the source of pressurized gas for driving the implant gun 50. Those skilled in the art will also recognize that any other type of portable pressurized gas source may be used to drive the implant gun 50. The cartridge 62 is adjustably retained within a non-removable engagement clip 64 having an external knurled knob 66. The non-removable engagement clip 64 defines a substantially conforming seat 68 which is operable to conformingly mate with the cartridge 62. The non-removable engagement clip 64 further includes a substantially cylindrical outer sidewall 70 that is rotatably retained within a bore 72 formed within the handle 54. The non-removable engagement clip 64 also includes an internally threaded sidewall 74 that threadably engages a threaded engagement sleeve 76 having a tubular engagement seat 78.

The engagement seat 78 engages the neck 80 of the cartridge 62 as the cartridge 62 is axially advanced upon rotating the knurled handle 66. While the neck 80 is shown as a substantially smooth cylindrical sidewall, a threaded neck may also be used that threadably engages a threaded engagement seat. Upon rotating the knurled knob 66, a tubular piercing member 82 pierces a seal within the neck portion 80 of the cartridge 62. The tubular piercing member 82 is rigidly retained by an engagement sleeve 84 adjacent an annular seal member 86. The cartridge 62 sealingly abuts the seal member 86 adjacent the sharpened tubular piercing member 82. Upon the seal being pierced, the pressurized gas having a stored energy passes through the piercing member 82 and into a cylindrical valve chamber 88 formed within a stepped cylindrical portion 90 of the tubular engagement seat 78. The pressurized gas within the valve chamber 88 pushes a valve plunger 92 having a plunger shaft 94 into an O-ring 96 to seal the valve chamber 88. The plunger shaft 94 extends through an orifice 98 that is sealed by the O-ring 96 and the valve plunger 92. The valve chamber 88 and the corresponding valve components are formed by or retained within a trigger housing 100.

The plunger shaft 94 extends within a notched region 106 formed within a trigger shaft 108. The trigger shaft 108 axially extends from the trigger 56 and is slidably retained within a trigger bore 110. The trigger shaft 108 is substantially cylindrical and includes a first annular groove 112 and a second annular groove 114, each retaining an O-ring 116. The O-rings 116 are used to seal the trigger shaft 108 relative to the trigger bore 110. Located adjacent to the trigger 56 is a safety member 118 which pivots about pin 120. Upon rotating a safety latch 122, the safety member 118 may be rotated into engagement with the trigger 56, thereby preventing the trigger 56 from being depressed. With the safety latch 122 non-engaged, depressing the trigger 56 results in the notch 106 of the trigger shaft 108 engaging the plunger shaft 94. This engagement causes the plunger 92 to become unseated from the O-ring 96 within the valve chamber 88.

Once the plunger 92 is unseated from the O-ring 96, the pressurized gas within the valve chamber 88 passes through the orifice 98 and travels between the trigger shaft 108 and the trigger bore 110 into delivery port 124 with the O-rings 116 retaining the gas within this region. The delivery port 124 is defined within the trigger housing 100 and a piston housing 126 that slidably retains a cylindrical piston 128. The piston housing 126 defines an elongated cylindrical bore 130 having a stepped region 132. The cylindrical bore 130 is sealed by way of a cylindrical plug 134 having an O-ring 136 within an annular groove 138. The plug 134 is retained within the bore 130, via a pin 140. The plug 134 further includes an angled or conically shaped end wall 142 forming or defining a gas charge chamber 144 located about the periphery of the end portion 146 of the piston 128.

The piston 128 includes the end portion 146, an O-ring 148 located within an annular groove 150 and a through window 152. The piston 128 further includes a stepped cylindrical nose 154 and a notched portion 156. Passing axially through a bore 158 defined within the piston 128 is a flexible drive rod or shaft 160 formed from stainless steel or any other appropriate material. The drive rod 160 is retained within the piston 128, via a threaded sidewall 162. The threaded sidewall 162 threadably engages a female member 164 within the window 152. An O-ring 166 is further provided about the drive rod 160, as well as a washer 168 that abuts with the female member 164. The O-ring 166 provides a level of shock absorption for the drive rod 160. The drive rod 160 extends out through a bore 170 formed within the housing 126. The bone 170 may include a gasket to seal the rod 160 relative to the bore 170. In this way, during arthroscopic surgery, irrigation fluid is substantially inhibited from entering the implant gun 50.

To insure a sufficiently high velocity of travel for the piston 128, the piston 128 is engagingly retained within the bore 130, via a release mechanism 172. The release mechanism 172 includes a roller 174 attached to a spring member 176 that is secured within a slot 178 formed within of the housing 126. The roller 174 is nestingly received within the notch 156 while a curved end 180 of the spring 176 is resiliently retained with a resilient flexible member 182. The resilient member 182 extends around the housing 126 at point 184, wraps around a pair of pins 186 extending out from the housing 126 and is looped about the end 180. The resilient member 182 in combination with the flexible metallic spring 176 resiliently retains the roller 174 within the notch 156 until a high enough pressure builds up within the chamber 144. Alternatively, another spring mechanism can be employed which utilizes a resilient material that is positioned dorsal to the spring 176. In this way, the resilient material is captured between the spring 176 and the body 52 which compresses under the force of the pressure applied to the piston 128. Once this pressure is reached, which is generally about 150 to 200 psi, this force upon the end 146 of the piston 128 causes the roller 174 to be unseated from the notch 156, thereby triggering the piston 128 within the bore 130. The triggering of the piston 128 drives the shaft 160 at a high velocity through the bore 170.

Figure 6:
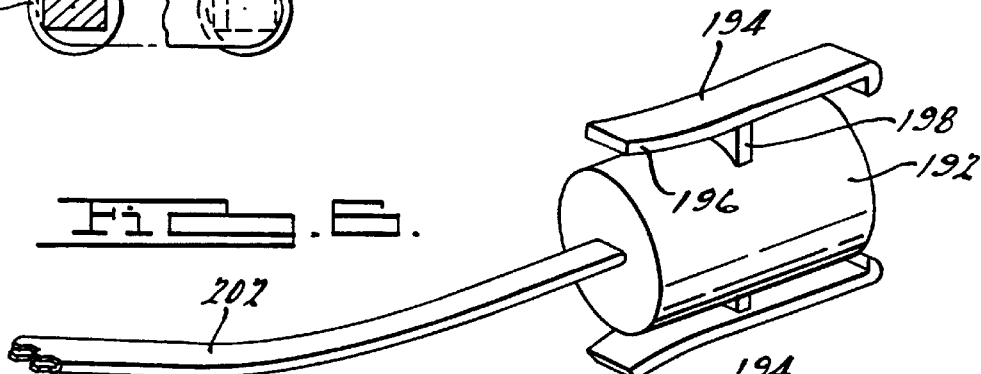
FIG. 6 is a perspective view of a quick disconnect shaft providing an upward or downward directed barrel.
Figure 7:
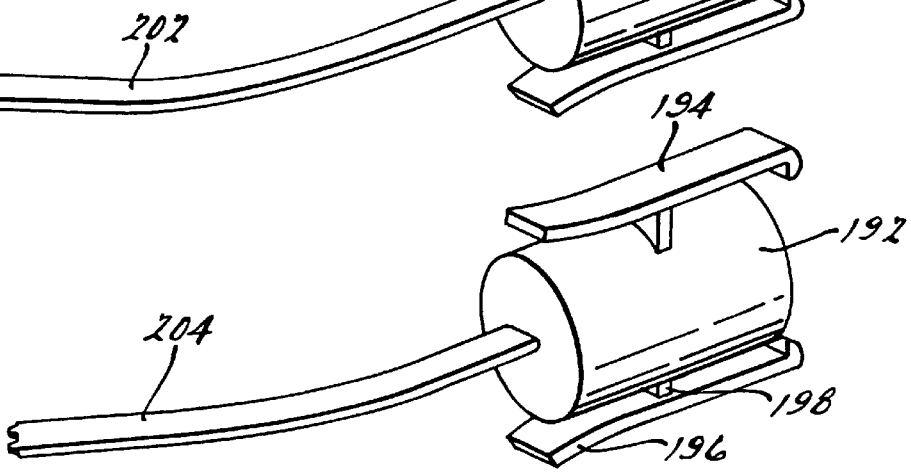
FIG. 7 is a perspective view of a quick disconnect shaft providing an right or left directed barrel.
Figure 4:
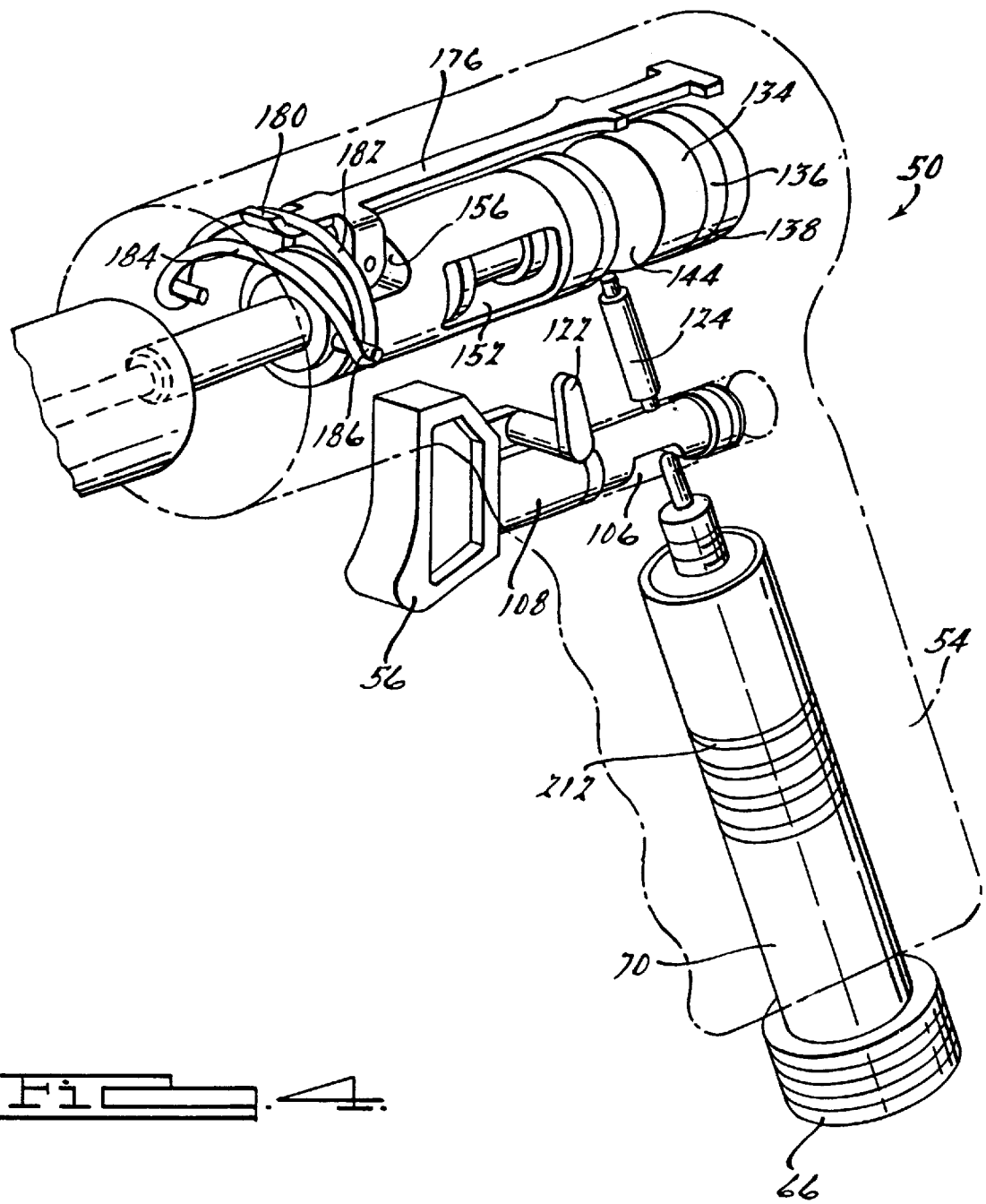
FIG. 4 is a perspective view of a pneumatic powered implant device according to the teachings of the present invention.

The shaft 160 extends within the elongated barrel 60 which is retained relative to the chuck 58, via a cylindrical seat 192 and a quick disconnect mechanism 194. The shaft 160 may include a centering mechanism, such as centering members attached to the shaft 160 about the center line of the shaft to insure that the shaft 160 travels appropriately down the barrel 60. To return the piston 128 to its original non-actuated position, a coil spring may be employed at the front end of the piston 128, whereby the actuated piston 128 will compress the spring so that the spring exerts a return force. The quick disconnect mechanism 194 includes a pair of flexible fingers 196 that are rigidly secured, via posts 198 within seat 192. A pair of latches 199 engage the chuck 58, thereby removably retaining the barrel 60 relative to the gun 50. The barrel 60, shown in FIG. 5 is a substantially straight oval shaped barrel 60 with the shaft 160 extending substantially along the entire length of the barrel 60, less about 15 mm at its distal end 200 for clearance and receipt of the surgical staple 10. Should a different shaped barrel be required depending on the location of the tear and the surgeon's desire, a curved barrel 202, as shown in FIG. 6, may be used that is curved upward or downward depending upon how the quick disconnect mechanism 194 is rotated relative to the gun 50. A right or left directed barrel 204, is shown in FIG. 7. In this regard, either the barrel 202 or the barrel 204 may be directed either upward or downward or left to right upon rotating the respective barrel 1800. This enables the surgeon to quickly and easily substitute different barrels depending upon the surgical requirements.

Turning now to FIGS. 8A–8E, the method of repairing a torn meniscus or any other type of soft tissue will be discussed. In this regard, it should be noted that the implant device 50 may be utilized to implant various types of surgical devices for repair or securement during different surgical procedures. Referring to FIG. 8A, a perspective view of the surgical staple 10 being loaded within the barrel 60 of the implant gun 50 is shown. A loading rod 206 is employed to push the surgical staple 10 into the barrel 60 and into frictional engagement with the distal end of the shaft 160. The shaft 160 includes a cradle 207 having a pair of fingers 208 that frictionally engage the notch regions 36 of the surgical staple 10. By engaging the surgical staple 10 at the notch regions 36, the force imparted upon the surgical staple 10 extends axially along each axis 42 of the legs 12 and 14. The cradle 207 further includes a center arm 209 having a semi-spherical protuberance 211. The arm 209 and the protuberance 211 engages the connection member 16 to further retain the surgical staple 10 within the barrel 60.

Once the surgical staple 10 is loaded into the barrel 60, as shown in FIG. 8A, the knurled knob 66 of the implant gun 50 is rotated to release the high pressure $CO_2$ gas from within the cartridge 62. Upon rotating the knurled knob 66, the clip 64 drives the cartridge 62 into piercing engagement with the piercing member 82, as a one-way spring retainer 210 engages notches 212 formed within clip 64. The spring retainer 210 prohibits the clip 64 from being removed from the gun 50. With the valve chamber 88 pressurized and the safety member 118 in place, the surgeon positions the barrel 60 adjacent to a tear 214 in a meniscus 216, as shown in FIG. 8B.

Once in position, the safety latch 122 is rotated to disengage the safety member 118, enabling the trigger 56 to be depressed. Upon depressing the trigger 56, the surgical staple 10 is driven into the meniscus 216 with each leg 12 and 14 positioned on opposite ends of the tear 214, as shown in FIGS. 8D–8E. As shown in FIG. 8A, the surgical fastener 10 is fully received within the barrel 60 until it is implanted or driven into the meniscus 216. As the surgical staple 10 is driven into the meniscus 216, via the shaft 160, the shaft 160 extends slightly beyond the barrel 60, as shown clearly in FIG. 8D. This enables the shaft 160 to drive the surgical fastener 10 fully into the meniscus 216, whereby to prevent the femoral condyle from contacting the surgical fastener 10. Additionally, since the shaft 160 extends slightly beyond the barrel 60 upon impacting the surgical staple 10, this provides the option for the surgeon to further seat and impact the surgical staple 10 by simply aligning the distal end 200 of the barrel 60 adjacent to the surgical staple 10 and engaging the trigger 56. Once engaged, the shaft 160 may again contact the surgical staple 10 as it extends beyond the barrel 60. With a typical $CO_2$ cartridge 62, approximately 10 to 15 discharges of the implant gun 50 will be available to the surgeon and approximately three (3) surgical fasteners 10 will be used in the repair procedure. Once the gas is expired, a surgeon will merely dispose of the implant gun 50.

The implant gun 50 will be sterilized and pre-packaged for the surgeon's use. In this way, a surgeon can simply open the package and remove the sterilized implant gun 50. The surgical staples 10 will also be sterilized and packaged in a single container generally containing one (1) to three (3) surgical staples, as well as the loading rod 206. Here again, the surgeon will simply open the package and remove the surgical staples 10 as needed during the surgical procedure. It should further be noted that the pneumatic powered implant gun 50 may be utilized to drive any type of implant into a patient. For example, the implant gun 50 may be used to implant and drive the surgical staple 10, suture anchors, surgical nails, dental implants, bone cement or caulking material, etc. The implant gun 50 may also may be used to compress and apply surgical rivets.

Turning to FIGS. 9–10, a pneumatic powered implant gun 240 according to the teachings of a second preferred embodiment in the present invention is shown. The implant gun 240 is substantially similar to the implant gun 50, except for the noted differences discussed herein. In this regard, the implant gun 240 also includes a body 242 having a handle 244, a trigger 246 and a chuck 248. Extending from the chuck 248 is a removable barrel 250 that is removably coupled to the chuck 248.

The pneumatic powered implant gun 240 is also powered by a $CO_2$ cartridge 252 which provides the source of pressurized gas for driving the implant gun 240. The cartridge 252 is threadably retained within the handle 244 by use of a conventional cartridge 252. The Cartridge 252 includes a threaded neck portion (not shown) that threadably engages a threaded engagement seat that is substantially similar to the engagement seat 78. To inhibit the pneumatic powered implant gun 240 from being used once the pressurized gas has been exhausted from the cartridge 252, the tubular piercing member used in the implant gun 240 which is substantially similar to the tubular piercing member 82 in the implant gun 50 is merely retained within the implant gun 240 by a press fit. Thus, upon piercing the seal in the cartridge 252 with the tubular piercing member, upon removing the cartridge 252, the tubular piercing member is also removed as it is held within the sealing portion of the cartridge 252. This inhibits further use of the disposable implant gun 240 once the useful life of the cartridge 252 has been used.

The chuck 248 and the removable barrel 250 of the implant gun 240 provide a quick disconnect mechanism 254 which is different from the implant gun 50. In this regard, the quick disconnect mechanism 254 includes a U-shaped lever 256 which may be rotated or flipped about pivot point 258 to lock and unlock the barrel 250. Specifically, referring to FIGS. 10A and 10B, the chuck 248 defines a cylindrical cavity 260 which seats an o-ring seal 262. The removable barrel 250 includes an elongated barrel 264 that slidably receives a drive shaft 266 and a tapered seat 268 that is captured within cylindrical cavity 260. The tapered seat 268 includes a first annular sidewall 270 and a second annular sidewall 272 with a tapered region 274 located therebetween. The annular region 270 defines a spherical contour 276 which provides assistance in guiding the drive shaft 266 within the elongated barrel 264.

Figure 10A:
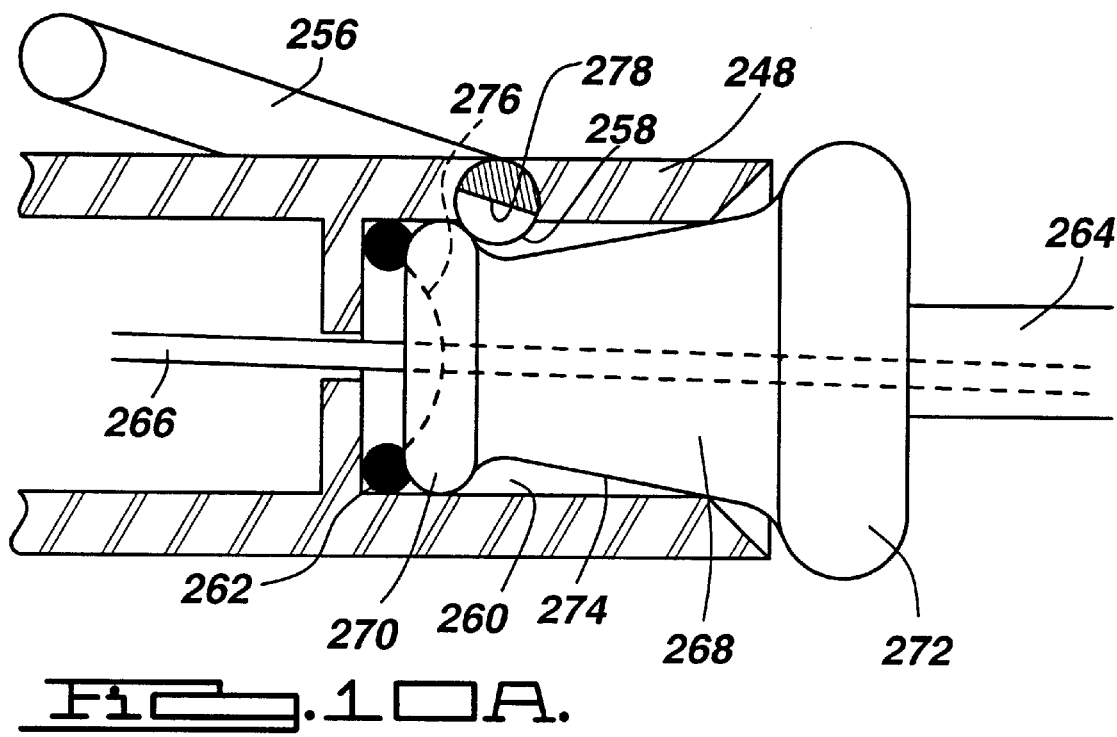
FIGS. 10A and 10B are side cross-sectional views of a quick disconnect shaft coupled to the pneumatic powered implant device of FIG. 9.
Figure 10B:
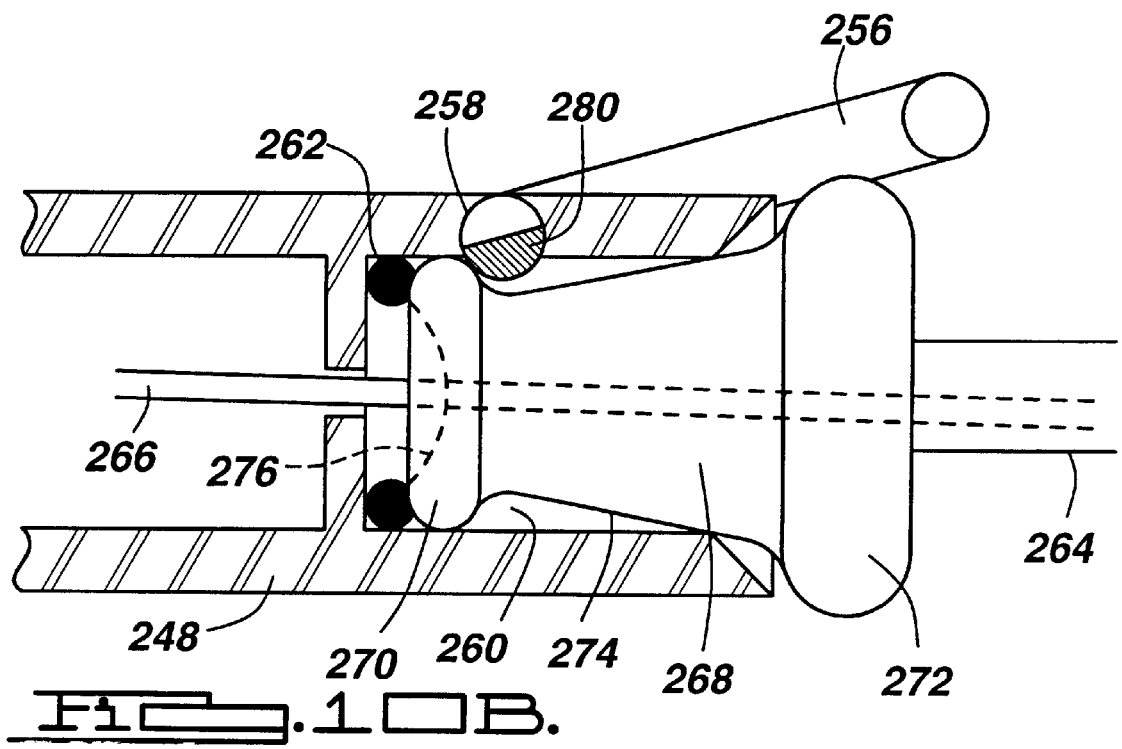

In use, the tapered seat 268 of the removable barrel 250 is slidably received within the cylindrical cavity 260 of the chuck 248 with the annular portion 270 engaging the o-ring seal 262. Once fully seated within the cavity 260, the lever 256 that is positioned in the unlocked location, shown in FIG. 10A, is pivoted approximately 180° to the lock position, shown in FIG. 10B. In the unlocked position, the lever 256 exposes a planar cutout region 278 in the cylindrical lever 256. This provides clearance for the tapered seat 268 to be slidably received within the cavity 260. Once the lever 256 is pivoted or rotated to its locked position, the cutout or planar region 278 is rotated approximately 180° to expose a cylindrical portion 280 of the lever 256. This cylindrical portion 280 retains the annular portion 270 against the o-ring seal 262 to removably retain the removable barrel 250 relative to the implant gun 240.

Figure 11:
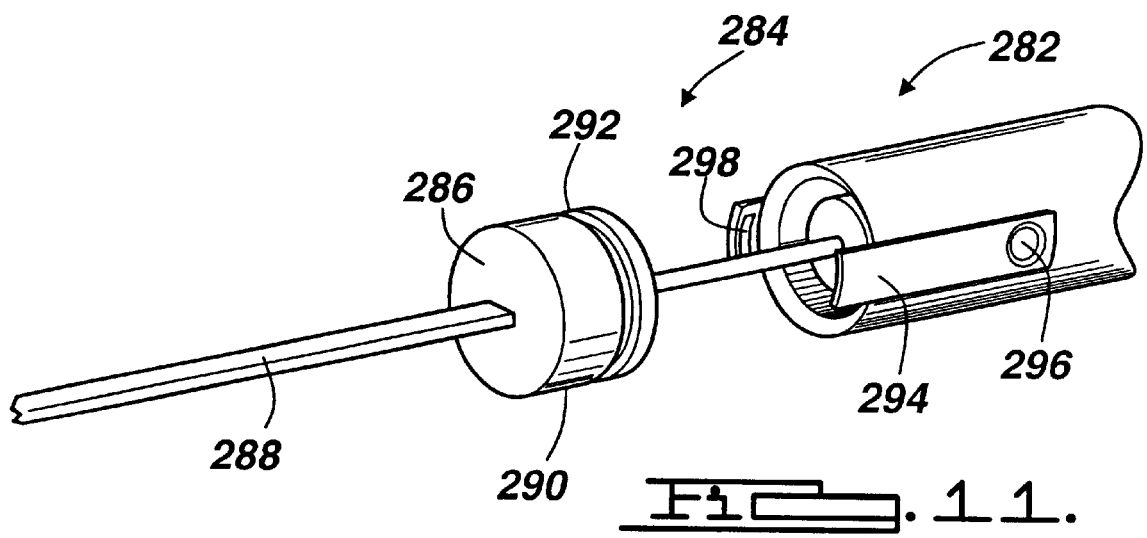
FIG. 11 is a partial perspective view of a shaft end of a pneumatic powered implant device according to the teachings of another preferred embodiment in the present invention.

Turning to FIG. 11, a partial perspective view of a pneumatic powered implant gun 282 according to the teachings of a third preferred embodiment is shown. In this regard, the implant gun 282 is substantially similar to the implant gun 50 except for the quick disconnect mechanism 284. In this regard, the removable barrel 286 includes an elongated barrel 288, along with a cylindrical seat 290. The cylindrical seat 290 defines an annular groove 292 which is removably engaged by a pair of flexible fingers 294 which are retained relative to the implant gun 282 by way of rivets 296 or other appropriate connection mechanisms. A pair of latches 298 located within the flexible fingers 294 snappingly engage the annular groove 292 to retain the removable barrel 286 relative to the implant gun 282. Here again, an appropriate o-ring seal or other sealing mechanism will be used to seal the cylindrical seat 290 relative to the implant gun 282 to insure that the pressurized gas is directed down the barrel 288. While Applicant has disclosed various quick connect mechanisms, it is further contemplated that other types of quick connect mechanisms may also be utilized to enable different shaped removable barrels to be easily and quickly engaged and disengaged from the pneumatic powered implant gun of the present invention.

Figure 12:
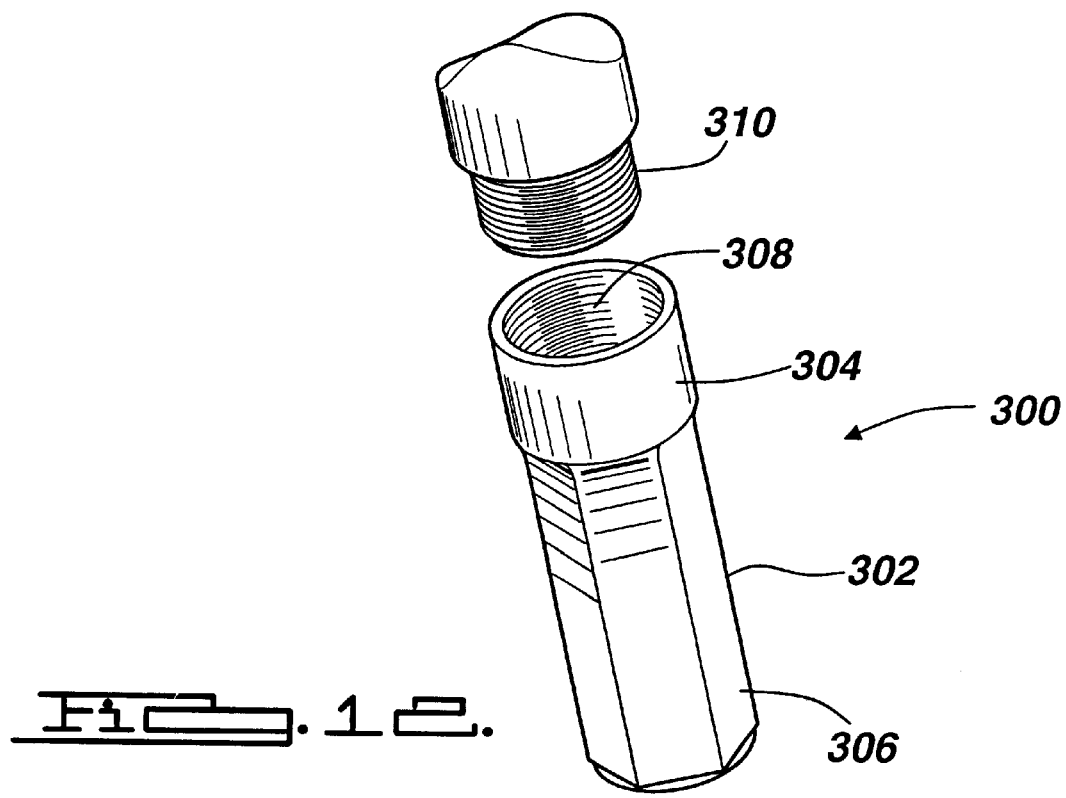
FIG. 12 is a partial perspective view of a handle of a pneumatic powered implant device according to the teachings of another preferred embodiment in the present invention.

Referring now to FIG. 12, a cut away portion of a pneumatic powered implant gun 300 according to the teachings of a fourth preferred embodiment in the present invention is disclosed. In this regard, the pneumatic powered implant gun 300 is substantially similar to the pneumatic powered implant gun 50, except that the $CO_2$ cartridge is not retained within a handle body 54, but forms the handle body itself. In other words, a cylindrical tube shaped handle 302 retains a $CO_2$ cartridge and forms the handle itself. The handle 302 includes threaded tubular portion 304 and a closed hexagonal or octagonal shaped portion 306. A cylindrical cavity 308 receives a $CO_2$ cartridge, while the handle 302 threadably engages a male threaded mating portion 310, extending from the implant gun 300, via the threaded tubular portion 304. Here again, the tubular piercing member for the implant gun 300 will merely be press fit to inhibit use of the implant gun 300 once the gas in the $CO_2$ cartridge has been fully used.

Referring to FIG. 13, an alternate embodiment for a cradle 312 according to the teachings of the present invention is disclosed. The cradle 312 is substantially similar to the cradle 207, except that the cradle 312 eliminates the fingers 208 and provides a cavity 314 for receipt of the surgical staple 10. The cradle 312 further includes a pair of hemispherical proturbences 316 opposed to one another which snappingly engage and retain the surgical staple 10 within the cradle 312.

The foregoing discussion discloses and describes merely exemplary embodiments of the present invention. One skilled in the art will readily recognize from such discussion, and from the accompanying drawings, that various changes, modifications and variations can be made therein without departing from the spirit and scope of the invention.

What is claimed is:

1. A pneumatic powered implant gun for driving an implant into a patient having a first leg, a second leg and a U-shaped connection member connecting the first leg relative to the second leg and having a pair of notch regions substantially centered along each longitudinal axis of the first and second legs, said pneumatic powered implant gun comprising:

a drive shaft operable to drive the implant into the patient;
   a cradle extending from a distal end of said drive shaft, said cradle operable to receive a portion of the U-shaped connection member to substantially impart a force axially from the pair of notch regions along each longitudinal axis of the first and second legs of the implant;
   a barrel that slidably receives said drive shaft, said barrel operable to guide the implant to a target site;
   a pressurized gas source operable to retain pressurized gas; and
   a trigger mechanism operable to release at least a portion of the pressurized gas, whereby upon said trigger mechanism being actuated, the pressurized gas drives said drive shaft along said barrel to drive the implant into the target site.

2. The pneumatic powered implant gun as defined in claim 1 wherein said pressurized gas source is a $CO_2$ cartridge.

3. The pneumatic powered implant gun as defined in claim 2 further comprising a handle operable to receive said $CO_2$ cartridge.

4. The pneumatic powered implant gun as defined in claim 1 further comprising a quick disconnect mechanism operable to disconnect said barrel from said pneumatic powered implant gun.

5. The pneumatic powered implant gun as defined in claim 4 wherein said quick disconnect mechanism includes at least one resilient finger.

6. The pneumatic powered implant gun as defined in claim 5 wherein said at least one resilient finger extends from said pneumatic powered implant gun.

7. The pneumatic powered implant gun as defined in claim 5 wherein said at least one resilient finger extends from said barrel.

8. The pneumatic powered implant gun as defined in claim 1 wherein said drive shaft further includes a mechanism operable to removably retain the implant.

9. The pneumatic powered implant gun as defined in claim 1 wherein said drive shaft extends beyond said barrel upon driving the implant into the patient to fully seat the implant within the patient at the target site.

10. A surgical staple for use in repairing tissue in a patient, said surgical staple comprising:

a first leg having a first proximal end and a first distal end, said first leg includes a spear member at said first distal end;
    a second leg having a second proximal end and a second distal end, said second leg includes a spear member at said second distal end, a substantially rectangular body extends from each of said spear members forming said first leg and said second leg; and
    a substantially rigid connection member operable to substantially retain said first leg relative to said second leg, said substantially rigid connection member being cylindrical in shape and having a transition region that transitions from said substantially rectangular shaped first leg and said substantially rectangular shaped second leg to said substantially cylindrical shaped rigid connection member, wherein upon implanting said surgical staple, said surgical staple is substantially inhibited from migration in the tissue.

11. A surgical staple for use in repairing tissue in a patient, said surgical staple comprising:

a substantially rectangular shaped first leg having a first proximal end and a first distal end;
    a substantially rectangular shaped second leg having a second proximal end and a second distal end; and
    a substantially rigid connection member operable to substantially retain said first leg relative to said second leg, said substantially rigid connection member being cylindrical in shape having a transition region that transitions from said substantially rectangular shaped first leg and said substantially rectangular shaped second leg to said substantially cylindrical shaped rigid connection member, wherein upon implanting said surgical staple, said surgical staple is substantially inhibited from migration in the tissue.

12. A surgical staple for use in repairing tissue in a patient, said surgical staple comprising:

a first leg having a first proximal end and a first distal end;
    a second leg having a second proximal end and a second distal end; and
    a substantially rigid connection member operable to substantially retain said first leg relative to said second leg, said substantially rigid connection member having a pair of notched regions substantially centered along a first longitudinal axis of said first leg and a second longitudinal axis of said second leg and being substantially U-shaped to retain said first leg substantially parallel to said second leg, wherein upon implanting said surgical staple, said surgical staple is substantially inhibited from migration in the tissue and an impact force is directed along each longitudinal axis of said first and second legs.

13. The surgical staple as defined in claim 12 wherein said first leg includes a conically shaped spear member at said first distal end and said second leg includes a conically shaped spear member at said second distal end.

14. The surgical staple as defined in claim 12 wherein said first leg and said second leg each include a plurality of barbs.

15. A surgical staple for use in repairing tissue in a patient, said surgical staple comprising:

a first leg having a first proximal end and a first distal end;

a second leg having a second proximal end and a second distal end; and a substantially rigid connection member operable to substantially retain said first leg relative to said second leg, said rigid connection member includes a pair of notch regions substantially centered along each longitudinal axis of said first leg and said second leg such that an impact force is directed from said notch regions along each longitudinal axis of said first leg and said second leg, wherein upon implanting said surgical staple, said surgical staple is substantially inhibited from migration in the tissue.

16. A method for driving an implant into a patient, said method comprising:

providing an implant having a first leg, a second leg and a substantially U-shaped connection member retaining the first leg relative to the second leg, and having a first notch region substantially centered along a first longitudinal axis of the first leg and a second notch region substantially centered along a second longitudinal axis of the second leg;

loading the implant within a barrel of a pneumatic powered implant gun;

engaging the implant along the first and second notch regions with a drive shaft slidably disposed within the barrel; and releasing pressurized gas to drive the drive shaft along the barrel to drive the implant along the first and second longitudinal axes into the patient.

17. The method as defined in claim 16 further comprising releasing pressurized gas from a $CO_2$ cartridge.

18. The method as defined in claim 16 further comprising driving a surgical staple into a torn meniscus.

* * * * *

UNITED STATES PATENT AND TRADEMARK OFFICE
CERTIFICATE OF CORRECTION

PATENT NO. : 6,387,113 B1
DATED : May 14, 2002
INVENTOR(S) : H. Gene Hawkins and David R. Sarver It is certified that error appears in the above-identified patent and that said Letters Patent is hereby corrected as shown below:

Column 3,
Line 4, "an" should be -- a --.

Column 5,
Line 57, "bone 170" should be -- bore 170 --.
Line 65, delete "of".

Column 6,
Line 44, "1800" should be -- 180º --.
Line 48, "tom" should be -- torn --.

Column 7,
Line 64, "Cartridge" should be -- cartridge --.

Signed and Sealed this

Twenty-fourth Day of December, 2002

JAMES E. ROGAN
*Director of the United States Patent and Trademark Office*